United States Patent
Tanaka et al.

(10) Patent No.: US 6,693,085 B2
(45) Date of Patent: Feb. 17, 2004

(54) MACROLIDE COMPOUND JK

(75) Inventors: Yasushi Tanaka, Chiba (JP); Hisayuki Komaki, Choshi (JP); Akira Nemoto, Hasaki-machi (JP); Katsukiyo Yazawa, Funabashi (JP); Yuzuru Mikami, Oamishirasato-machi (JP)

(73) Assignee: Higeta Shoyu Co., Ltd., Tokyo (JP)

( * ) Notice: Subject to any disclaimer, the term of this patent is extended or adjusted under 35 U.S.C. 154(b) by 176 days.

(21) Appl. No.: 09/926,403

(22) PCT Filed: Feb. 23, 2001

(86) PCT No.: PCT/JP01/01363
§ 371 (c)(1),
(2), (4) Date: Oct. 26, 2001

(87) PCT Pub. No.: WO01/64700
PCT Pub. Date: Sep. 7, 2001

(65) Prior Publication Data
US 2003/0069193 A1 Apr. 10, 2003

(30) Foreign Application Priority Data
Mar. 1, 2000 (JP) ......................... 2000-056538

(51) Int. Cl.$^7$ ......................... A01N 43/04; A61K 31/70; C07H 15/00; C07H 17/00; C07H 17/02
(52) U.S. Cl. ......................... 514/27; 514/33; 536/4.1; 536/16.8; 536/16.9; 536/17.2; 536/18.1; 536/18.2; 536/18.4; 536/18.5; 536/29.1
(58) Field of Search ......................... 514/27.33; 536/4.1, 536/17.2, 18.1, 18.2, 18.4, 18.5, 16.8, 16.9, 29.1

(56) References Cited

U.S. PATENT DOCUMENTS 5,096,817 A 3/1992 Nishio et al.

FOREIGN PATENT DOCUMENTS

| EP | 0 345 078 | 12/1989 |
| EP | 0 398 588 | 11/1990 |

OTHER PUBLICATIONS

Ashton et al., "MM 46115, a New Antiviral Antibiotic from *Actinomadura pelletieri*", The Journal of Antibiotics, vol. 43, No. 11, pp. 1387–1393, 1990.*

R. J. Aston, et al., The Journal of Antibiotics, vol. 43, No. 11, pps. 1387–1393, "MM46115, A New Antiviral Antibiotic from *Actinomadura pelletieri* Characteristics of the Producing Cultures, Fermentation, Isolation, Physico–Chemical and Biological Properties", 1990.

K. Luk, et al., J. Chem. Soc. Perkin Trans. 1, vol. 7, pps. 1641–1644, "Structural Studies of MM46115, A Novel Tetronic Acid Containing Macrolide with Antiviral and Antibacterial Activity Isolated Form *Actinomadura pelletieri*", 1991.

I. Momose, et al., The Journal of Antibiotics, vol. 52, No. 9, pps. 781–786, "Decatromicins A and B, New Antibiotics Produced by Actinomadura Sp. MK73–NF4 I. Taxonomy, Isolation, Physico–Chemical Properties and Biological Activities", Sep. 1999.

I. Momose, et al., The Journal of Antibiotics, vol. 52, No. 9, pps. 787–796, "Decatromicins A and B, New Antibiotics Produced by Actinomadura Sp. MK73–NF4 II. Structure Determination", Sep. 1999.

* cited by examiner

*Primary Examiner*—James O. Wilson
*Assistant Examiner*—Traviss C. McIntosh, III
(74) *Attorney, Agent, or Firm*—Oblon, Spivak, McClelland, Maier & Neustadt, P.C.

(57) ABSTRACT

Compound JK represented by the general formula (1):

wherein R is H or —CH$_3$;
or a pharmaceutically acceptable salt thereof.

Compound JK has an excellent antimicrobial activity even against resistant strains including MRSA and is useful as an anti-microbial agent.

17 Claims, 1 Drawing Sheet

(1)

(wherein R is H or -CH₃)

MACROLIDE COMPOUND JK

TECHNICAL FIELD

The present invention relates to novel compound JK. More particularly, it relates to novel compounds JK-1 and JK-2, and a process for producing them, and use of them. The novel compounds JK-1 and 2, which are so far unknown novel macrolide compounds isolated from microorganisms, particularly from a culture of actinomycetes, have excellent physiological activities, particularly potent antimicrobial effect, especially activity against MRSA (methicillin-resistant *Staphylococcus aureus*). Known MM46115, which is analogous to the compounds of the invention (R. J. Ashton et al., J. Antibiot., Vol. 43, 1387–1393 (1990); K. Luk et al., J. Chem. Soc. Perkin Trans. 1, Vol. 7, pp. 1641–1644 (1991)), exhibits strong cytotoxicity, whereas the novel compounds JK-1 and JK-2 are characterized in that they do not have cytotoxicity at all. Further study has to be continued to elucidate the detailed mechanisms, though it is presumed as a mechanism that the $CH_3$ group at 3' position is important for generation of the cytotoxicity due to structural difference.

Therefore, the novel macrolide compounds JK-1 and JK-2 of the invention are very useful as antimicrobials in preventive and/or therapeutic agents, which can be effectively utilized. The compounds of the invention have potent antimicrobial activities and are not only effective against MRSA (methicillin-resistant *Staphylococcus aureus*) which has become a problem in recent years, but also much more active against MRSA than currently employed vancomycin. In addition to these characteristics, they have no problem on safety and show a distinctive feature in practical use.

PRIOR ART

A large number of novel compounds have been discovered and synthesized as antimicrobial agents, some of which have been put to practical use. On the other hand, since multiple-drug resistant strains have occurred as represented by hospital-acquired infection, a new type of antimicrobial agents which have a different active site from that of the existing antimicrobial agents and are effective against the resistant strains have been required.

Though a variety of superior antimicrobial agents have long been known, it has been required to develop antimicrobial agents which are effective against MRSA and other resistant strains and highly appreciated in safety and productivity.

PROBLEMS THAT THE INVENTION IS TO SOLVE

The present invention was made in response to such demands in this field. In this situation, extensive screenings were conducted along the technological trend of development of antimicrobial agents and consequently it was found that so far unknown novel compounds had anti-microbial activities. The present invention was completed based on these findings. The purpose of the present invention is to provide novel antimicrobial compounds that are much better than the known compounds in antimicrobial activities against various microorganisms including resistant strains, safety such as no toxicity and no side effects, and productivity such as easy mass production.

MEANS FOR SOLVING THE PROBLEMS

In order to obtain novel antimicrobial compounds, the present inventors searched widely natural products, particularly metabolites of microorganisms, to reach more effective antimicrobials. As a result, they found materials that have the aimed action in the cell extract of an actinomycete, *Actinomadura pelletieri* IFM0903 (FERM BP-7030). They investigated physicochemical properties of the materials to reveal the chemical structures, and confirmed that the materials are so far unknown and novel. As described in Claims 1 to 3, the materials are novel macrolide compounds as shown by the general formula (1). The inventors have designated these compounds generally JK, and specifically one JK-1 in which R in the formula (1) is a methyl group and the other JK-2 in which R is a hydrogen atom.

That is, the present invention relates to novel compound JK of the formula (1) as shown in FIG. 1 (which involve JK-1 wherein $R=CH_3$ and JK-2 wherein $R=H$) or a pharmaceutically acceptable salt thereof.

In the present invention, the salt includes all of pharmaceutically acceptable salts, for example, alkali metal salts such as sodium salts, potassium salts, etc., alkaline earth metal salts such as calcium salts, magnesium salts, etc., inorganic acid salts such as hydrochloride, sulfate, nitrate, etc., and organic salts such as organic acid salts, amine salts, pyridinium salts, etc.

In addition, the present invention relates to an antimicrobial agent comprising as the effective component a novel macrolide compound JK-1, JK-2 or a pharmaceutically acceptable salt thereof. The present invention will be explained in detail hereinafter.

MODE FOR CARRYING OUT THE INVENTION

Figure 1:
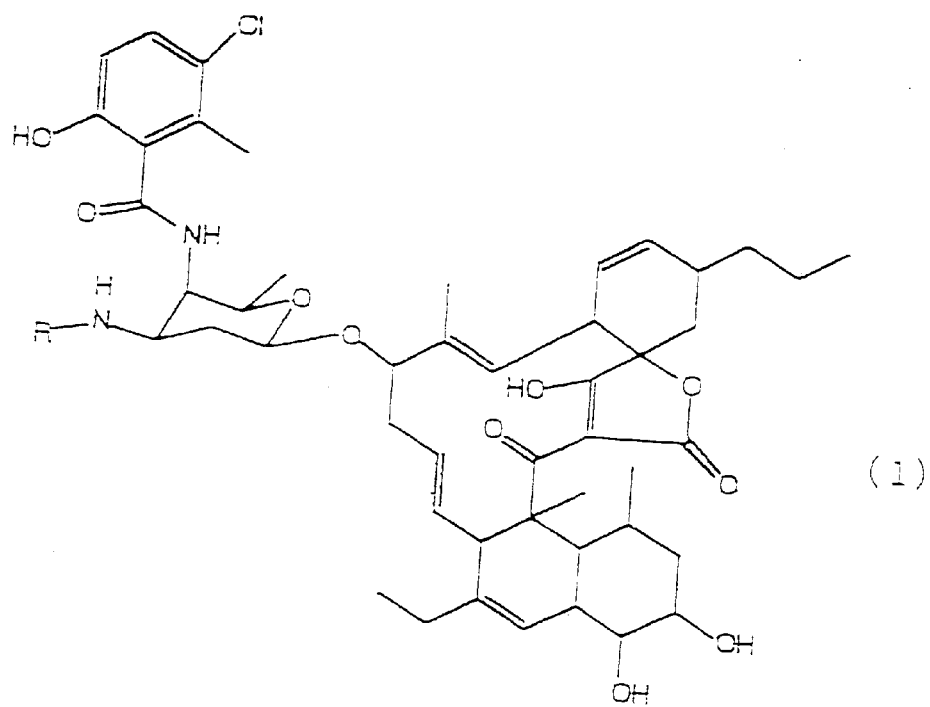
FIG. 1 shows the chemical structure of the novel compound JK of the general formula (1).

The compound JK of the present invention is a mixture, from which 2 kinds of compounds, i.e., JK-1 and JK-2, have been isolated at present. Among these compounds, the following table 1 shows the physicochemical properties of JK-1.

Table 1

Table 1. Physicochemical properties of JK-1

(1) Color and Appearance: colorless powder
(2) IR spectrum: the followings are significant signals.
  $IR_{vmax}$ ($cm^{-1}$, in KBr):
  813, 936, 977, 1006, 1030, 1058, 1094, 1122, 1180, 1219, 1289, 1312, 1343, 1375, 1404, 1453, 1456, 1504, 1580, 1618, 1690, 1723, 1753, 2950, 3425
(3) UV spectrum:
  $UV_{\lambda max}$ (nm, MeOH): 235, 280 ($\epsilon$ 11000)
(4) Molecular weight: 877
(5) Molecular Formula: $C_{49}H_{66}N_2O_{10}Cl$
(6) Mass spectrum
  HREIMS m/z
  Found: 877.4425 (M+)
  Calculated: 877.4440 ($C_{49}H_{66}N_2O_{10}Cl$)
(7) Specific Rotation:
  $[\alpha]_D$ (MeOH, C=0.15%) −141.5°

In the $^1H$ NMR and $^{13}C$ NMR spectra of the compound JK-1, the following table 2 lists significant signals.

Table 2

TABLE 2

Chemical Shifts of JK-1
(δ in ppm, J in Hz)

| Position | $\delta_H$, J | $\delta_C$ | HMBC ($^1$H) |
|---|---|---|---|
| 1 | — | 166.8 | — |
| 2 | — | 105.6 | — |
| 3 | — | 208.7 | 27 |
| 4 | — | 53.7 | 27, 13 |
| 5 | 3.8 dd, 3, 3 | 38.0 | 27, 10 |
| 6 | 1.9 m | 30.4 | 28, 5, 7 |
| 7 | 1.65 m/1.77 m | 39.9 | 28, 8 |
| 8 | 4.02 m | 69.9 | 9, 7 |
| 9 | 3.50 dd, 2, 11 | 75.15 | 8, 10 |
| 10 | 2.20 m | 40.9 | 5 |
| 11 | 5.63 d, 10 | 119.1 | 10, 29 |
| 12 | — | 138.5 | — |
| 13 | 2.22 d, 7 | 57.2 | 14, 29 |
| 14 | 5.51 dd, 12, 7 | 132.8 | 13, 15 |
| 15 | 5.05 dd, 12, 4, 2 | 127.1 | 16, 14 |
| 16 | 2.24 m/2.32 m | 36.4 | 15, 17 |
| 17 | 3.82 dd, 2, 2 | 84.5 | 31, 16, 1' |
| 18 | — | 141.6 | 31, 19 |
| 19 | 4.82 d, 9 | 123.2 | 31, 20 |
| 20 | 3.60 dd, 10, 7 | 42.1 | 19, 21 |
| 21 | 5.39 dd, 10, 5 | 123.8 | 22, 20 |
| 22 | 5.75 dd, 5, 10 | 132.4 | 21, 23 |
| 23 | 2.70 m | 34.0 | 32, 22, 24 |
| 24 | 1.87 dd, 13, 1 | 36.9 | 23, 32 |
| 25 | — | 84.7 | 24, 21 |
| 26 | — | 199.9 | 24, 21 |
| 27 | 1.19 d, 6 | 16.7 | 5 |
| 28 | 0.64 d, 7 | 19.9 | 6 |
| 29 | 1.80 m/1.96 m | 27.5 | 30 |
| 30 | 0.94 t, 7 | 12.45 | 29 |
| 31 | 1.69 s | 11.5 | 17 |
| 32 | 1.3–1.4 m | 37.8 | 22 |
| 33 | 1.3–1.4 m | 19.7 | 34 |
| 34 | 0.91 t, 7 | 14.2 | 33 |
| 1' | 4.43 dd, 11, 2 | 98.8 | 2' |
| 2' | 1.32 m/2.0 m | 31.7 | 1' |
| 3' | 2.28 m | 64.0 | 4', 2', 7' |
|    | 2.85 br (NH) | — | — |
| 4' | 4.49 dd, 11, 3 | 48.5 | 3', 5', 4'-NH |
|    | 6.04 d (NH) | — | — |
| 5' | 3.58 m | 70.4 | 6' |
| 6' | 1.26 d, 7 | 17.3 | 5' |
| 7' | 2.37 br | 43.1 | — |
| 1" | — | 125.18 | 8" |
| 2" | — | 133.7 | 8" |
| 3" | — | 125.0 | 8" |
| 4" | 7.21 d, 7 | 131.2 | 5" |
| 5" | 6.67 d, 7 | 116.2 | 4" |
| 6" | — | 153.1 | — |
| 7" | — | 167.5 | 5'($^4$J Weak) 4'-NH |
| 8" | 2.34 | 17.2 | — |

Moreover, the compound JK-2 was also analyzed by means of FAB-MS and HR-FAB-MS to measure the molecular weight, and its structural formula as described in Claims was deduced from the presumed molecular formula. The result is as follows.

JK-2 $C_{48}H_{63}N_2O_{10}Cl$ (863)

The compound JK is produced by, for example, *Actinomadura pelletieri* IFM0903 (FERM BP-7030).

Microbiological characteristics of *Actinomadura pelletieri* IFM0903 areas follows. When cultured on an oatmeal agar medium (ISP-3), it has branched long hyphae and aerial hyphae as seen in a species of Actinomycetes morphologically. When the incubation time is prolonged, several bacillus-like spores, fragmentation of aerial hyphae and fragmentation of vegetative hyphae were observed. Since the fragmentation of vegetative hypae was observed, it was assumed morphologically to belong to Actinomadura.

Table 3 below shows the cultural characteristics of *Actinomadura pelletieri* IFM0903 on a variety of culture media. Table 4 below shows physiological and biochemical characteristics.

Table 3

TABLE 3

Cultural characteristics of *Actinomadura pelletieri* IFM0903

| Culture Medium | Characteristics |
|---|---|
| ISP-1 (Trypton/yeast extract agar) | good growth, wrinkle on surface, pale brown, no aerial hyphae, occurrence of brown soluble pigment |
| ISP-2 (Yeast/malt agar) | good growth, wrinkle on surface, slight red, no aerial hyphae, occurrence of dark brown soluble pigment |
| ISP-3 (Oatmeal agar) | moderate growth, smooth surface, light red, no aerial hyphae, no soluble pigment |
| ISP-5 (Glycerol/asparagine agar) | good growth, wrinkle on surface, pale orange, no aerial hyphae, occurrence of light pink soluble pigment |
| ISP-7 (Tyrosine agar) | good growth, wrinkle on surface, pale orange, no aerial hyphae, occurrence of light pink soluble pigment |
| BHI (Brain-heart infusion agar) | moderate growth, wrinkle on surface, colorless, no aerial hyphae, no soluble pigment |
| NB (Nutrient agar) | good growth, wrinkle on surface, reddish pink, no aerial hyphae, occurrence of dark red soluble pigment |

Table 4

TABLE 4

Physiological and biochemical characteristics of *Actinomadura pelletieri* IFM0903

| Decomposition | |
|---|---|
| Adenine | negative |
| Casein | negative |
| Hypoxanthine | negative |
| Tyrosine | negative |
| Xanthine | negative |
| Acid formation from sugar | |
| Galactose | negative |
| Glucose | positive |
| Inositol | negative |
| Rhamnose | negative |
| Maltose | negative |
| Adonitol | negative |
| Arabinose | negative |
| Erythritol | negative |
| Mannose | negative |
| Sorbitol | negative |
| Sensitivity against Antibiotics | |
| Imipenem | positive |
| Tobramycin | positive |
| 5-FU | positive |
| Kanamycin | positive |
| β-Lactamase formation | positive |
| Growth at 45° C. | Growing |

Said strain was incubated in a culture medium (brain heart infusion containing 2% glucose) under shaking of 250 rpm (stirring) at 30° C. for 72 hours, the cells growing in the medium were collected by centrifugation (3000 rpm×10 minutes) and washed twice with distilled water. The cells were further washed with ethanol, and then dried in vacuo to give dry cells. The dry cells were analyzed for the constitution of amino acids, sugars and lipids of the cell wall according to Bergey's Manual of Determinative Bacteriology 9th ed., Williams, Baltimore, 1993. The result of amino acid analysis indicated the presence of meso-diaminopimelic acid, and sugar analysis detected madurose. As the lipid constitution of the cells, an isoprenoid quinone, MK-9(H6) was confirmed as a major component. Moreover, said strain was identified to be *Actinomadura pelletieri* from assimilation of adenine, casein, hypoxanthine and tyrosine as shown in Table 4 as well as from the formation pattern of acid from sugars.

Thus, said strain was classified into *Actinomadura pelletieri* and distinctively characterized by production of the compound JK. Accordingly, said strain was designated as *Actinomadura pelletieri* IFM0903 as new strain and internationally deposited at National Institute of Bioscience and Human-Technology, National Institute of Advanced Industrial Science and Technology (FERM BP-7030).

The compound JK of the present invention is produced by *Actinomadura pelletieri* IFM0903 (FERM BP-7030). In addition, the production of compound JK has been confirmed in other strains of Actinomadura. The present invention, accordingly, includes use of a wide variety of variants which can produce the compound JK, including variants naturally mutated and variants artificially mutated, acquired by treatment with mutagens such as X-ray irradiation, γ-ray irradiation, nitrogen mustard, N-methyl-N'-nitro-N-nitroso-guanidine, 2-aminopurine, ethyl methanesulfonate, etc.

The novel compound JK represented by the formula (1) in the present invention may be produced by means of chemical syntheses as well as by microorganisms as mentioned above.

In the latter case, the novel compound JK of the formula (1) in the present invention can be produced by incubating a strain of Actinomadura producing said compounds, for example, *Actinomadura pelletieri* IFM0903, in a culture medium containing assimilative carbon source and nitrogen source, preferably in an aerobic submerged culture condition (e.g., shaking, aeration and agitation, etc.).

As the carbon source, glucose, glycerol, sucrose, starch, dextrin, and other carbohydrates can preferably be used.

As the nitrogen source, oatmeal, yeast extract, beef extract, tuna extract, peptone, gluten meal, cotton seed oil, soybean meal, corn steep liquor, dry yeast, wheat embryo, peanut flour, chicken bone and meat meal, and the like can preferably be used. Inorganic and organic nitrogen compounds such as ammonium salts (e.g., ammonium nitrate, ammonium sulfate, ammonium phosphate, etc.), urea, amino acids, and the like may be used effectively.

These carbon sources and nitrogen sources may be used favorably in combination, though in using they are not necessarily in a pure form. The reason is that it is desirable to use the impure source since it contains growth factors or trace elements.

If necessary, it may be employed to add an inorganic salt such as sodium carbonate, potassium carbonate, sodium phosphate, potassium phosphate, sodium chloride, potassium chloride, sodium iodide, potassium iodide, magnesium salt, copper salt, cobalt salt, and the like, to the culture medium.

If necessary, particularly when the medium is foaming, it may be employed to add an antifoaming agnet such as liquid paraffin, animal oil, vegetable oil, mineral oil, silicone, and the like.

In order to produce the aimed material in large quantities on an industrial scale, the incubation may preferably be conducted under aeration and agitation in the same manner as in other products by fermentation. In production on a small scale, it is preferable to carry out the incubation with shaking using flasks.

When the incubation is conducted in a large tank, in order to prevent delay of growth of the cells during the production of the compound JK, it is preferred to inoculate and incubate the cells for production once in a small amount of the medium, and then transfer the culture into a large tank and incubate for large scale production.

In this case, the medium used in the preliminary culture may be the same as that used in the production culture, or if necessary both may be altered.

The culture may preferably be conducted under aeration and agitation, in which the agitation may be carried out by a known method, for example, with a propeller or other mechanical means, by rotation or shake of a fermenter, use pump processing, aeration, etc. Air for aeration is preferably sterilized.

The incubation temperature may properly be changed within a range in which the compound JK can be produced, and the incubation is usually carried out at 10–40° C., preferably at 25–35° C.

The incubation time depends on the culture condition or the volume of culture, and is usually about 1 day to about 1 week.

After the fermentation has been finished, the aimed compound JK is recovered from the culture. Briefly, the cells are extracted directly with water and/or an organic solvent, or they may be destructed by a known means such as mechanical destruction or ultrasonication followed by extraction with water and/or an organic solvent, and the product may be recovered and purified in a conventional method. When the culture is liquid, it may be extracted directly with a solvent or separated by filtration or centrifugation. The liquid is then condensed under reduced pressure, lyophilized, pH-adjusted, and contacted with and adsorbed on a carrier such as anion or cation exchange resin, active carbon, powdered cellulose, silica gel, alumina, adsorptive resin, etc., from which the product is eluted.

As the recovery and purification method, a conventional method(s) for recovering antibiotics is(are) suitably used, including extraction with water, organic solvent or a mixture thereof; chromatography; recrystallization from a single solvent or a mixture of solvents; or a combination thereof.

The recovery and purification of the compound JK may be conducted properly by a conventional method(s) described above, for example, as follows.

First, the culture is applied to centrifugation or treatment with an MF membrane to collect the cells, which are extracted with methanol, and the extract is condensed and further extracted with diethyl ether. The ether extract is condensed under reduced pressure, chromatographed on silica gel, then stepwise and/or continuously eluted with hexane and ethyl acetate. The pure fraction may be evaporated to dryness under reduced pressure, then further fractionated by HPLC (ODS column), and evaporated to dryness.

When the compound JK of the present invention is administered as a medicament, it may be administered as such or as a pharmaceutical composition containing, for example, 0.1%–99.5%, preferably 0.5%–90% of the compound JK in a pharmaceutically non-toxic and inactive carrier.

As the carrier, one or more of solid, semi-solid or liquid diluents, fillers, and other auxiliaries for formulation may be used. The pharmaceutical composition may be administered preferably in a form of dosage unit. The pharmaceutical composition of the present invention may be administered orally, via tissue, locally (percutaneously, etc.), or rectally, or it may be used as an agent for external application. It may, of course, be administered as a preparation suitable for its administration method.

The dose as an antimicrobial may preferably be determined in consideration of the condition of the patient such as age, body weight, etc., administration route, character and severity of disease, and the like. In general, the effective dose of the compound of the invention is in a range of 10–2000 mg a day for an adult. The above dose is sometimes enough, and contrary in some case it has to be increased. When a large amount is required, it is desirable to administer it in divided doses several times a day and/or continuously. Even though the compound JK was orally administered to rats at a daily dose of 500 mg, no acute toxicity was observed even after lapse of 10 days. Thus, safety was recognized.

For oral administration, a solid or liquid dosage unit preparation, for example, powder, mixed powder, tablet, sugar coated tablet, capsule, drop, sublingual tablet, and the like may be used.

Powder may be prepared by pulverizing the active material in an appropriate particle size. Mixed powder may be produced by pulverizing the active material into suitable fineness followed by mixing with similarly pulverized pharmaceutical carrier, for example, edible carbohydrate such as starch, mannitol, and the like. If necessary, flavor, preservative, dispersing agent, coloring agent, aromatic, and the like may be added.

Capsule may be prepared by filling pulverized dust or powder or granules into capsule shells such as gelatin capsule. It is also possible to mix the powdered material with a lubricant or fluidizing agent, for example, colloidal silica, talc, magnesium stearate, calcium stearate, solid polyethylene glycol, followed by filling operation. Disintegrator or solubilizing agent, for example, carboxymethylcellulose, calcium carbonate, sodium carbonate, etc. may be added in order to improve efficacy of the drug after intake of capsules.

Moreover, fine powder of the compounds may be suspended or dispersed in vegetable oil, polyethylene glycol, glycerin, or surfactant, and wrapped with gelatin sheets to prepare a soft capsule.

Tablet may be prepared by making a powdered mixture, forming granules or slags, then adding a disintegrator or lubricant thereto, and subjecting the resulting mixture to tabletting.

The powdered mixture may be prepared by mixing the properly powdered compound with the above-mentioned diluent or base, and if necessary using a binder (e.g., sodium carboxymethylcellulose, alginate salt, gelatin, polyvinylpyrrolidone, polyvinyl alcohol, etc.), dissolution-delaying agent (e.g., paraffin, etc.), reabsorbing agent (e.g., quaternary salt) and/or adsorbing agent (e.g., bentonite, kaolin, dicalcium phosphate, etc.) in combination. The powdered mixture can be prepared into granules, by moistening the mixture with a binder such as syrup, starch paste, gum Arabic, cellulose solution or macromolecule solution, and subsequently passing the mixture through a screen in an enforcing manner. Alternatively, the powder is applied directly to a tabletting machine not through granulation, and the resulting slags of incomplete forms are pulverized into granules.

Thus prepared granules can be prevented from adhering each other by adding a lubricant such as stearic acid, stearate, talc, mineral oil, and the like. Thus lubricated mixture is then tabletted. Alternatively, the drug which has been combined with a mobile inactive carrier, may be tabletted directly without forming granules or slags. Transparent or translucent protective coating comprising shellac closed coating, coating made of sugar or macromolecular material, or polished coating comprising wax, may also be used.

Other oral-type preparations such as solution, syrup and elixir may also be formulated into a dosage unit containing a certain amount of the compound. Syrup may be prepared by dissolving the compound in a suitable flavor aqueous solution. Elixir may be prescribed by dispersing the compound into a non-toxic alcoholic carrier. If necessary, a solubilizing agent or emulsifying agent (e.g., ethoxylated isostearyl alcohols, polyoxyethylene sorbitol esters), preservative, flavoring agent (e.g., peppermint oil, saccharin), and the like may be added.

If necessary, the dosage unit formulation for oral administration may be formed into microcapsules. This formulation may be coated or implanted in a macromolecular compound or wax to prolong the action period or produce the sustained release.

For parenteral administration, liquid dosage unit preparation as subcutaneous, intramuscular or intravenous injection, for example, solution or suspension may be used. These preparations may be prepared by suspending or dissolving a certain amount of the compound in a non-toxic liquid carrier adaptable for injection use, for example, aqueous or oily medium, and then sterilizing the resulting suspension or solution. Alternatively, a certain amount of the compound may be placed in a vial, which after sterilization of the contents may be tightly closed. In order to dissolve or mix the contents immediately before administration, spare vial or carrie may be provided along with the powdered or lyophilized effective component. For isotonicity adjustment of the injections, a non-toxic salt or salt solution may be added. Furthermore, a stabilizer, a preservative, an emulsifying agent, and the like may be used together.

For rectal administration, suppository may be used which is prepared by mixing the compound with a low-melting solid, such as polyethylene glycol, cacao butter, higher ester (e.g., myristyl palmitate) and a mixture thereof. It may be applied directly to the affected part as an external preparation.

The present invention will be explained, hereinafter, in more detail by the following examples, which are not intended as a limitation thereof.

EXAMPLE 1

(1) Fermentative Production

*Actinomadura pelletieri* IFM 0903 (FERM BP-7030) was inoculated on 25 ml of 2% glucose-added brain heart infusion liquid medium (made by Difco Co.) dispensed into 50 ml Erlenmeyer flasks, and incubated at 30° C. with shaking for 72 hours. The thus-obtained culture (2 ml each) was then inoculated in 200 ml of the same medium dispensed into 500 ml Erlenmeyer flasks, and the same preliminary incubation was conducted. The thus-obtained preliminary culture (1.5 L) was inoculated on 15 L of a medium (pH 7.0) for production containing 2% glucose, 0.5% meat extract (Wako Pure Chem. Ind., Ltd.), 0.5% Polypepton P1, 0.5% Polypepton (Nihon Pharmaceutical Co., Ltd.), and 0.3% sodium chloride, placed in a 20 L fermentation tank, and incubated at 28° C. under aeration (15 L/minute) and agitation (200 rpm) for 90 hours.

(2) Recovery and Purification

The resulting culture (15 L) was filtered through a filter cloth to recover the cells. To the cells was added 3 L of methanol for extraction, and the extract was condensed in an evaporator. Distilled water (300 ml) was added to the condensate, followed by partition extraction 3 times with 1 L of ethyl acetate. The ethyl acetate fraction (3 L) was evaporated to dryness in an evaporator and applied to silica gel column chromatography (column size: 3 cm×20 cm). The column was eluted stepwise with 1 L each of n-hexane/ethyl acetate (40:1, 20:1, and 5:1). Then, the eluate was purified by preparative reverse phase HPLC. Detection of the compound JK in the eluate was achieved by a paper disc method using *Micrococcus luteus*. Each active fraction recovered was evaporated to dryness in an evaporator to give 13 mg of the compound JK-1 and 3.5 mg of JK-2.

EXAMPLE 2

Cytotoxicity

Two cultured tumor cell lines of human origin, HL-60 and L1210, were used as follows for determining cytotoxicity of the compound JK.

The compounds JK-1 and JK-2 separately were dissolved in methanol, which were then diluted serially, separately, with the culture media to give JK solutions in a series of concentration. The respective cell suspensions ($5 \times 10^4$ cells/ml) were prepared by suspending lymphocyte malignant cells HL-60 and L1210, separately, in an RPMI1640 medium (containing 10% bovine serum). The JK solution (20 µl) and the cell suspension (180 µl) were dispensed into a 96 well microplate, and incubated at 37° C. in a wet condition of 5% $CO_2$ and 95% air. After 72 hours, growth of the cells was measured by a colorimetric assay using 3-(4,5-dimethylthiazol-2-yl)-2,5-diphenyltetrazorium bromide (MTT). Namely, 20 µl each of 2 mg/ml-MTT solution was added to each well, and incubated at 37° C. for 4 hours. The formazan crystals formed in the cells were dissolved by adding 50 µl of 20% sodium dodecylsulfate prepared with 50% dimethylformamide solution, and the absorbance as an index of growth was measured at 570 nm using a microplate reader (immunoreader). From the following equation, a growth inhibition rate was calculated, and 50% growth inhibition concentration ($IC_{50}$ value) was obtained from the relation of the sample concentration to the inhibition rate.

Inhibition Rate (%)=(1−Q)×100 wherein Q=Absorbance after addition of sample/Absorbance with no sample addition The result indicated that the compounds JK-1 and JK-2 showed no cytotoxicity to lymphocytic malignant cell lines, of which the $IC_{50}$ value was >100 µg/ml.

EXAMPLE 3

Antimicrobial Activity

Antimicrobial activity of JK-1 was determined by measuring the minimum growth inhibition concentration (MIC) as follows.

MIC values of JK against a variety of microorganisms were determined on a Mueller-Hinton broth containing 0.2% glucose according to the rule of Japanese Society of Chemotherapy (Kouseibussitsu Taiyo (The Essentials of Antibiotics), 4th ed., University of Tokyo Press, 1992).

JK-1 was dissolved in methanol, and diluted with the above medium, repeating 2-fold dilution starting from 1 mg/ml. Test microorganisms were added to the above medium to give a test solution of $1 \times 10^6$ cells/ml. The JK solution (20 µl) and the test solution (180 µl) were dispensed in a 96 well microplate and incubated at 37° C. After 24 hours, either positive or negative growth was confirmed visually, and the MIC value was caluculated. The results are shown in the following table 5 and table 6.

Table 5

TABLE 5

Antimicribial Activity of JK-1

| Test Microorganim | MIC values (µg/ml) |
|---|---|
| Nocardia asteroides | 0.05 |
| Gordonia bronchialis | 0.39 |
| Staphylococcus aureus 209P | 0.05 |
| MRSA | 0.05 |
| Bacillus subtilis PCII89 | 0.39 |
| Micrococcus luteus | 0.05 |
| Corynebacterium xerosis | 0.025 |
| Escherichia coli NIH JC-2 | >100 |
| Asperigillus niger | >100 |
| Candida albicans | >100 |

Table 6

TABLE 6

Anti-MRSA Activity of JK-1 and 2
MIC values (µg/ml)

| Organism | JK-1 | JK-2 | a | b | c |
|---|---|---|---|---|---|
| S-1 | 0.78 | 0.78 | >100 | >100 | 6.25 |
| S-2 | 0.39 | 0.78 | 12.5 | >100 | 3.13 |
| S-3 | 0.39 | 0.39 | >100 | >100 | 1.56 |
| S-4 | 0.2 | 0.39 | >100 | >100 | 1.56 |
| S-5 | 0.2 | 0.2 | >100 | >100 | 1.56 |
| 3666 | 0.2 | 0.2 | >100 | >100 | 1.56 |
| 3667 | 0.2 | 0.2 | >100 | >100 | 3.13 |
| 3668 | 0.2 | 0.2 | >100 | >100 | 1.56 |
| 3669 | 0.2 | 0.2 | >100 | >100 | 0.78 |
| 3670 | 1.56 | 0.78 | >100 | >100 | 0.78 |
| 3671 | 0.1 | 0.2 | >100 | >100 | 0.78 | a: erythromycin; b: penicillin-G; c: vancomycin

The result indicated that JK-1 showed strong antimicrobial activities against gram-positive bacteria, i.e., MIC values of 0.025–0.39 µg/ml. No antimicrobial activity was observed against gram-negative bacteria and fungi. Among gram-positive bacteria, there was no difference between MIC values, especially, of *Staphylococcus aureus* and its multi-drug resistant strain MRSA (Table 5) which have become a clinical problem. In this situation, the antimicrobial activity of JK-1 was compared to that of commercially available 3 drugs in 11 strains of clinically freshly isolated MRSAs. The result indicated that JK-1 was about 6 times as active as an MRSA specific drug, vancomycin (Table 6).

EXAMPLE 4

Formulation

The following raw materials, (1) 20 g of the compound JK prepared in Example 1, (2) 80 g of lactose, (3) 30 g of corn starch, and (4) 2 g of magnesium stearate were formulated into tablets. Briefly, (1), (2) and (3)(15 g at this time) were mixed, and to the mixture were added (3)(5 g at this time) and (4), following by mixing well. The resulting mixture was pressed with a compressed tabletting machine to yield 800 tablets containing 25 mg/tablet of the effective component (1).

EFFECTS OF THE INVENTION

The present invention provides the compound JK, which is novel and exhibits excellent physiological activities. It is useful in various pharmaceutical preparations, for example, as antimicrobial agents effective against antibiotic resistant bacteria including MRSA which is posing more of a problem with hospital-acquired infection in recent years (more effective than vancomycin) as well as other-type antimicrobial agents.

Reference to the Deposit of a Microorganism under Rule 13-2 of Patent Cooperation Treaty
1. *Actinomadura pelletieri* IFM0903
  (a) Name and Address of the depositary authority at which the microorganism was deposited:
    Name: National Institute of Bioscience and Human-Technology, National Institute of Advanced Industrial Science and Technology
    Address: 1-3 Higashi 1 chome, Tsukuba-shi, Ibaraki-ken, Zip Code 305-0046 Japan
  (b) Date of Deposit on which the deposit was made at the authority of (a):
    Feb. 15, 2000
  (c) Accession Number of the deposit given by the authority of (a):
    FERM BP-7030

What is claimed is:

1. A compound represented by formula (1):

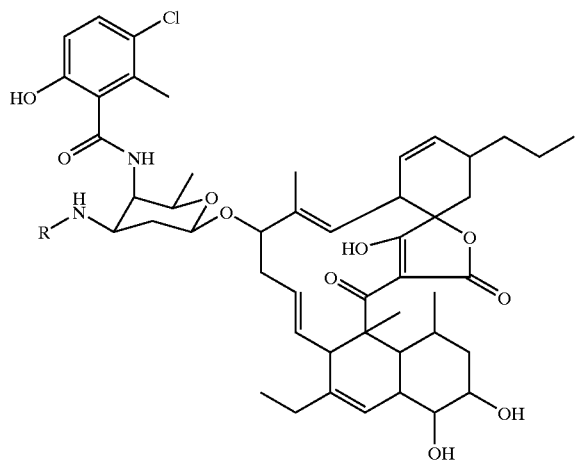

(1)

wherein
  R is H or —$CH_3$;
or a salt thereof.

2. The compound of claim 1, wherein R is —$CH_3$.

3. The compound of claim 1, wherein R is H.

4. The compound of claim 1 in the form of a pharmaceutically acceptable salt.

5. The compound of claim 1 in the form of an alkali metal salt.

6. The compound of claim 1 in the form of an alkaline earth metal salt.

7. The compound of claim 1 in the form of an inorganic acid salt.

8. The compound of claim 1 in the form of an organic acid salt.

9. The compound of claim 1 in the form of an amine salt.

10. The compound of claim 1 in the form of a pyridinium salt.

11. A composition comprising the compound of claim 1 and a carrier.

12. A sustained released preparation comprising the compound of claim 1 and a carrier.

13. A method for inhibiting the growth of a gram-positive bacterium comprising contacting said bacterium with an amount of the compound of claim 1 effective to inhibit its growth.

14. The method of claim 13, wherein said bacterium is Staphylococcus.

15. The method of claim 13, wherein said bacterium is *Staphylococcus aureus*.

16. The method of claim 13, wherein said bacterium is methicillin-resistant *Staphylococcus aureus* ("MRSA").

17. A method for producing the compound of claim 1 or a salt thereof, comprising:
  culturing a strain of Actinomadura which produces said compound for a time and under conditions suitable for production of said compound, and
  recovering said compound or a salt thereof.

* * * * *